(12) United States Patent
Ferree

(10) Patent No.: US 7,341,590 B2
(45) Date of Patent: Mar. 11, 2008

(54) HINGED ANTERIOR THORACIC/LUMBAR PLATE

(75) Inventor: Bret A. Ferree, Cincinnati, OH (US)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 10/860,850

(22) Filed: Jun. 3, 2004

(65) Prior Publication Data

US 2004/0225290 A1  Nov. 11, 2004

Related U.S. Application Data

(62) Division of application No. 10/108,287, filed on Mar. 27, 2002, now Pat. No. 6,764,489.

(60) Provisional application No. 60/279,157, filed on Mar. 27, 2001.

(51) Int. Cl.
*A61B 17/56* (2006.01)
*A61B 19/00* (2006.01)

(52) U.S. Cl. .................. 606/69; 128/898; 606/61

(58) Field of Classification Search .............. 606/71, 606/69, 70, 90; *A61B 17/70*
See application file for complete search history.

(56) References Cited

U.S. PATENT DOCUMENTS

| | | | |
|---|---|---|---|
| 4,448,191 A | 5/1984 | Rodnyansky et al. | |
| 5,242,443 A | 9/1993 | Kambin | |
| 5,681,311 A | 10/1997 | Foley et al. | 606/61 |
| 5,772,681 A | 6/1998 | Leoni | |
| 5,840,440 A | 11/1998 | Ovshinsky et al. | |
| 5,954,722 A | 9/1999 | Bono | 606/61 |
| 5,968,047 A * | 10/1999 | Reed | 606/76 |
| 6,030,389 A | 2/2000 | Wagner et al. | 606/71 |
| 6,280,445 B1 | 8/2001 | Morrison et al. | 606/61 |
| 6,331,179 B1 * | 12/2001 | Freid et al. | 606/61 |
| 6,432,106 B1 | 8/2002 | Fraser | |
| 6,458,131 B1 | 10/2002 | Ray | |
| 6,565,571 B1 | 5/2003 | Jackowski et al. | |
| 6,599,292 B1 * | 7/2003 | Ray | 606/90 |
| 2002/0099386 A1 * | 7/2002 | Beger et al. | 606/104 |
| 2002/0143336 A1 | 10/2002 | Hearn | 606/69 |

FOREIGN PATENT DOCUMENTS

| | | |
|---|---|---|
| DE | 9219204 | 12/1999 |
| WO | WO97/22306 | 6/1997 |
| WO | WO2006109132 | * 10/2006 |

* cited by examiner

*Primary Examiner*—Cris Rodriguez
*Assistant Examiner*—Candice C Stokes
(74) *Attorney, Agent, or Firm*—Jonathan D. Spangler

(57) ABSTRACT

An anterior thoracic/lumbar system comprising a thin plate and fasteners for securing the plate to vertebrae or other osseous material. The plate may be hinged along the central axis, with a pair of collinear holes on each portion of the plate. Each of the holes accommodates a bolt which is screwed into the vertebrae and secured to the plate using a nut.

81 Claims, 15 Drawing Sheets

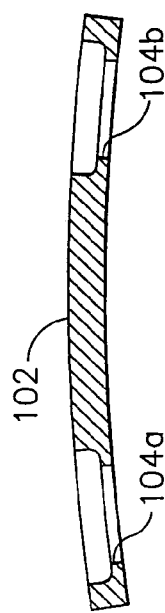
FIG. 19
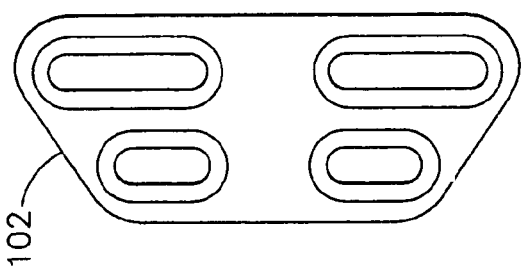
FIG. 22
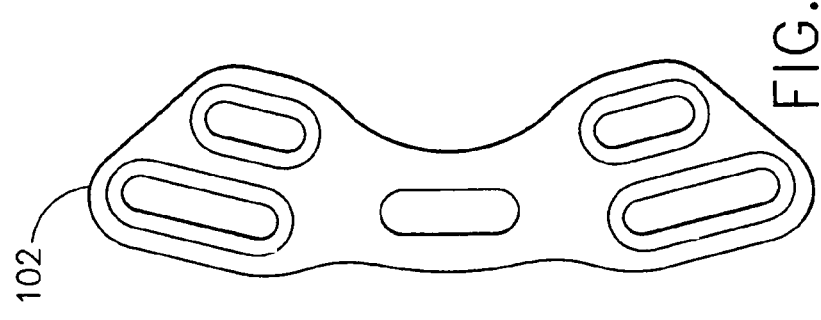
FIG. 21
FIG. 20

HINGED ANTERIOR THORACIC/LUMBAR PLATE

CROSS REFERENCES TO RELATED APPLICATIONS

The present application is a divisional of commonly owned and U.S. patent application Ser. No. 10/108,287 filed Mar. 27, 2002, now U.S. Pat. No. 6,764,489 the complete disclosure of which is hereby incorporated herein by reference in its entirety for all purposes. Additionally, the present application claims benefit under 35 U.S.C. § 119(e) from U.S. Provisional Application Ser. No. 60/279,157, filed on Mar. 27, 2001, the entire contents of which are hereby expressly incorporated by reference into this disclosure as if set forth fully herein.

BACKGROUND OF THE INVENTION

I. Field of the Invention

This invention relates generally to devices for use in spinal surgery, and, in particular, to a hinged anterior thoracic/lumbar plate which is implantable within a patient for stabilization of the spine.

II. Description of the Related Art

Eighty-five percent of the population will experience low back pain at some point. Fortunately, the majority of people recover from their back pain with a combination of benign neglect, rest, exercise, medication, physical therapy, or chiropractic care. A small percent of the population will suffer chronic low back pain. The cost of treatment of patients with spinal disorders plus the patient's lost productivity is estimated at 25 to 100 billion dollars annually.

Seven cervical (neck), 12 thoracic, and 5 lumbar (low back) vertebrae form the normal human spine. Intervertebral discs reside between adjacent vertebra with two exceptions. First, the articulation between the first two cervical vertebrae does not contain a disc. Second, a disc lies between the last lumbar vertebra and the sacrum (a portion of the pelvis).

Motion between vertebrae occurs through the disc and two facet joints. The disc lies in the front or anterior portion of the spine. The facet joints lie laterally on either side of the posterior portion of the spine. The osseous-disc combination of the spine coupled with ligaments, tendons, and muscles are essential for spine function. The spine allows movement (flexation, lateral bending, and rotation), supports the body, and protects the spinal cord and nerves.

The disc changes with aging. As a person ages the water content of the disc falls from approximately 85 percent at birth to 70 percent in the elderly. The ratio of chondroitin sulfate to keratin sulfate decreases with age. The ratio of chondroitin 6 sulfate to chondroitin 4 sulfate increases with age. The distinction between the annulus and the nucleus decreases with age. These changes are known as disc degeneration. Generally disc degeneration is painless.

Premature or accelerated disc degeneration is known as degenerative disc disease. A large portion of patients suffering from chronic low back pain is thought to have this condition. As the disc degenerates, the nucleus and annulus functions are compromised. The nucleus becomes thinner and less able to handle compression loads. The annulus fibers become redundant as the nucleus shrinks. The redundant annular fibers are less effective in controlling vertebral motion. The disc pathology can result in: 1) bulging of the annulus into the spinal cord or nerves; 2) narrowing of the space between the vertebrae where the nerves exit; 3) tears of the annulus as abnormal loads are transmitted to the annulus and the annulus is subjected to excessive motion between vertebrae; and 4) disc herniation or extrusion of the nucleus through complete annular tears. Disc herniation can also cause arthritis of the facet joints, which, in turn, may cause back pain.

The problems created by disc degeneration, facet arthritis, and other conditions such as spondylolysis, spondylolisthesis, scoliosis, fracture, tumor, or infection are frequently treated by spinal fusion. Such problems may include pain in the back or legs, nerve injury, risk of future nerve injury, or spinal deformity. The goal of spinal fusion is to successfully "grow" two or more vertebrae together. To achieve this, bone from the patient's body (spine or iliac crest) or from cadavers is grafted between vertebrae. Alternatively, bone graft substitutes, such as hydroxyapatite and bone morphogenetic protein, may be used. The bone graft is placed between the vertebrae in the disc space and/or over the posterior elements of the vertebrae (lamina and transverse processes). The surgeon scrapes the vertebrae to create bleeding. Blood flows into the bone graft. The scraped bone, blood clot (hematoma), and the bone graft simulates a fracture. As the patient heals, the "fracture" causes the vertebrae to be fused and heal together.

Spinal instrumentation may be placed onto or into the spine to immobilize the vertebrae that are going to be fused. Immobilization leads to a higher fusion rate and speeds a patient's recovery by eliminating movement. The use of spinal fixation plates or rods for correction of spinal deformities and for fusion of vertebrae is well known. Typically, a rigid plate is positioned to span bones or bone segments that need to be immobilized with respect to one another. Bone screws may be used to fasten the plate to the bones. Spinal plating systems are commonly used to correct problems in the lumbar and cervical portions of the spine, and are often installed posterior or anterior to the spine.

One technique of treating these disorders is known as surgical arthrodesis of the spine. This can be accomplished by removing the intervertebral disk and replacing it with bone and immobilizing the spine to allow space to connect the adjoining vertebral bodies together. The stabilization of the vertebrae to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function.

Several types of anterior spinal fixation devices are currently in use. One technique involves placement of screws completely through the vertebral body, called bicortical purchase. The screws are placed through a titanium plate but are not attached to the plate. This device is difficult to place, and over-penetration of the screws can result in damage to the spinal cord. The screws can back out of the plate into the surrounding tissues as they do not fix to the plate. Several newer generation devices have used a unicortical purchase of the bone, and in some fashion locking the screw to the plate to provide stability and secure the screw from backout. Problems have resulted from over rigid fixation and stress shielding, resulting in nonunion of the bony fusion, chronic micromotion during healing, resulting in stress fracture of the fixation device at either the screw to the plate resulting in screw backout, or inadequate fixation strength and resultant collapse of the graft and angulation of the spine.

Another technique involves formation of a medical construct using surgical rods and connectors. Such systems include a pair of rods which are placed on opposite sides of the portion of the spine which is intended to be fused. Pedicle, lateral, and oblique mounting means are used to secure the rods relative to the desired portion of the spine which will be fused by the fixation system. However, this construct extends outwardly further than a plate/screw system, potentially affecting the surrounding muscle, and causing pain to the patient.

Plates and screws are often placed onto the anteriolateral portion of the spine to facilitate spinal fusion. Generally, they are placed across one or two disc spaces in the treatment of fractures and tumors. Most of the present systems use screws with nuts for the posterior portion of the vertebrae. The screws with nuts are commonly called bolts by those skilled in this art. Screws, without nuts, are placed through the anterior portion of the plate. The posterior bolts are generally thought to rigidly fix the plate to the screws. Some surgeons believe that the rigid bolt/plate construct provides more spinal stability. However, while screws without nuts are easier to insert, they also are known to back out, causing potential failure of the fusion. Devices have been devised to hold the screws within the plate. It is believed that there are no systems in the marketplace which uses an all bolt construct.

A typical device which is used for spinal fixation is taught in U.S. Pat. No. 4,611,581. This device consists of a simple plate having a series of openings for receiving threaded portions of force transmitting members which securely lock in a part of the bone of the vertebra in which they are mounted and a threaded portion which projects outwardly from the vertebrae. The vertebra is pulled into the desired relationship with adjacent vertebrae by tightening a nut on the outwardly projecting end portion of the force transmitting member.

Another typical device used is shown in U.S. Pat. No. 6,306,136. This patent discloses an implant which is used particularly as an anterior cervical plate, having a solid plate consisting of two sliding parts, each of which has holes for anchoring screws in two adjacent vertebrae. The sliding parts are provided with a screw and slot for limiting the sliding travel between the parts.

Another vertebrae connecting plate is taught in U.S. Pat. No. 5,147,361. This plate has a small thickness, and uses set screws which are screw engaged in threaded holes within the connecting plate to prevent any loosening of the screws within the plate.

SUMMARY OF THE INVENTION

It is therefore an object of the present invention to provide a plate system for spinal surgery, which has a low profile and comfortably fits a patient's anatomy.

It is a further object of the present invention to provide a plate system which is easily implanted within a patient.

It is a further object of the present invention to provide a plate system which is easily positioned and establishes a secure connection between vertebrae.

It is a still further object of the present invention to provide a plate system which is easily adaptable to the lumbar/thoracic region of the spine.

These and other objects and advantages of the present invention will be readily apparent in the description that follows.

BRIEF DESCRIPTION OF THE DRAWINGS

FIG. 19 is a cross-sectional view of the plate shown in FIG. 17;

FIG. 20 is a plan view of a plate of the present invention which is angled for use on a kyphotic spine;

FIG. 21 is a plan view of a plate of the present invention which is angled for use on a lordotic spine; and FIG. 22 is a plan view of another embodiment of a spine plate according to the present invention.

DETAILED DESCRIPTION OF THE PREFERRED EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The hinged anterior thoracic/lumbar plate disclosed herein boasts a variety of inventive features and components that warrant patent protection, both individually and in combination.

Figure 2:
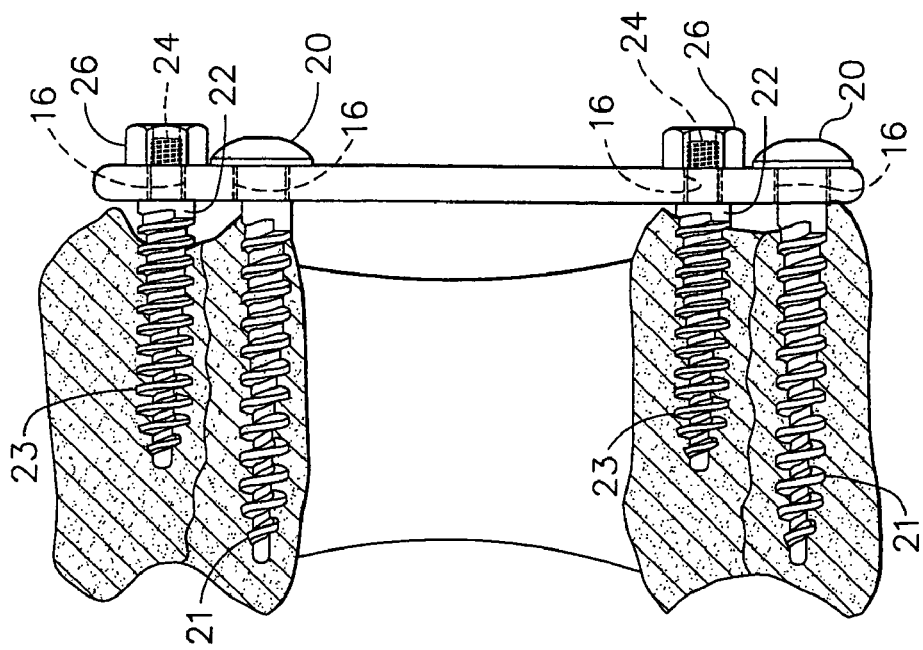
FIG. 2 is an anterior to posterior view of the plate shown in FIG. 1.
Figure 1:
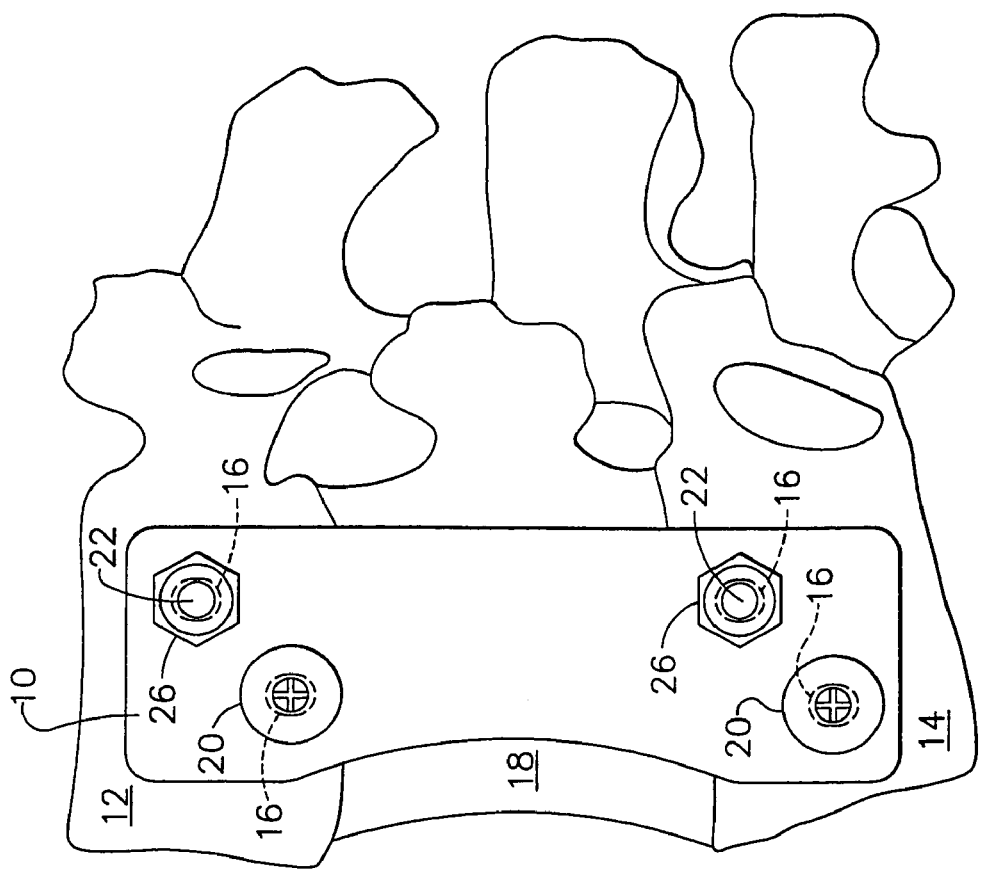
FIG. 1 is a lateral view of a prior art spinal plate installed in vertebrae of a spine.
Figure 4:
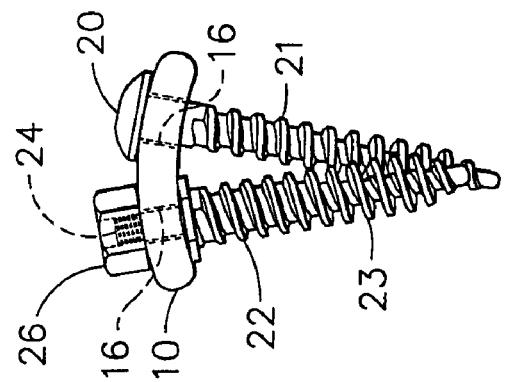
FIG. 4 is an end view of the plate and devices of FIG. 3 in the assembled position.
Figure 3:
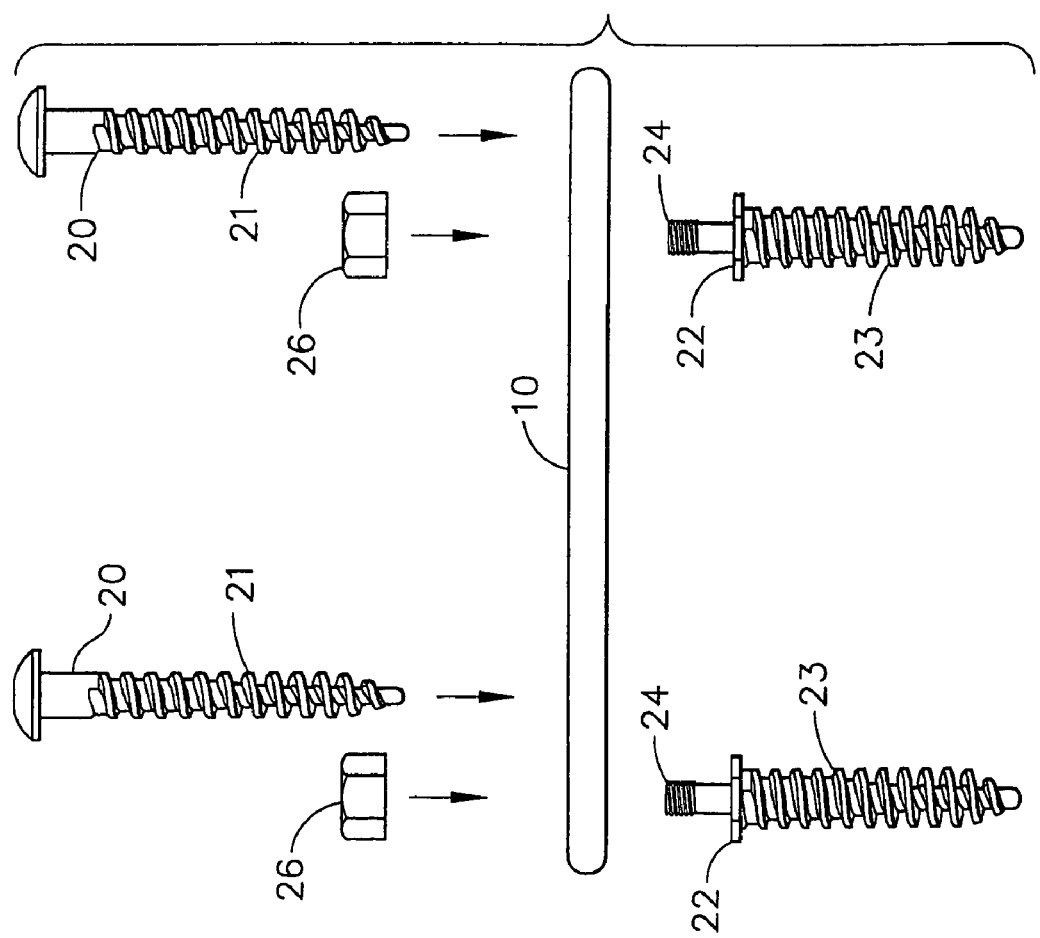
FIG. 3 is an exploded lateral view of the plate and associated devices shown in FIG. 1.

Spinal plate systems using a combination of screws and bolts to attach plates to the posterior portion of vertebrae are well known and commonly used in the prior art. FIGS. 1-4 depict one such common prior art method of spinal stabilization system, comprising a spinal plate 10 placed across several vertebrae 12, 14. Plate 10 contains a series of openings 16 which are intended to receive bone anchoring hardware. Two openings 16 are positioned against vertebra 12, and two openings 16 are positioned against vertebra 14. A bone graft 18 positioned between vertebrae 12, 14 acts as a replacement for a damaged or otherwise removed vertebra. A pair of screws 20, each having a threaded section 21, are installed through openings 16 on the anterior portion of plate 10, while a pair of bolts 22 are installed through openings 16 on the posterior portion of plate 10. Each bolt 22 consists of a lower threaded section 23 and an upper threaded post 24 to which a nut 26 is affixed to secure bolt 22 in position. The threaded sections 21, 23 of screws 20 and bolts 22 are anchored in vertebrae 12, 14. When installed in the spine, bolts 22 and screws 20 converge to resist pull-out, as shown in FIG. 4. This screw and bolt combination provides increased spinal stability, as the bolts 22 rigidly affix the spinal plate 10 to the screws 20, which are much easier to insert in the procedure.

Figure 5:
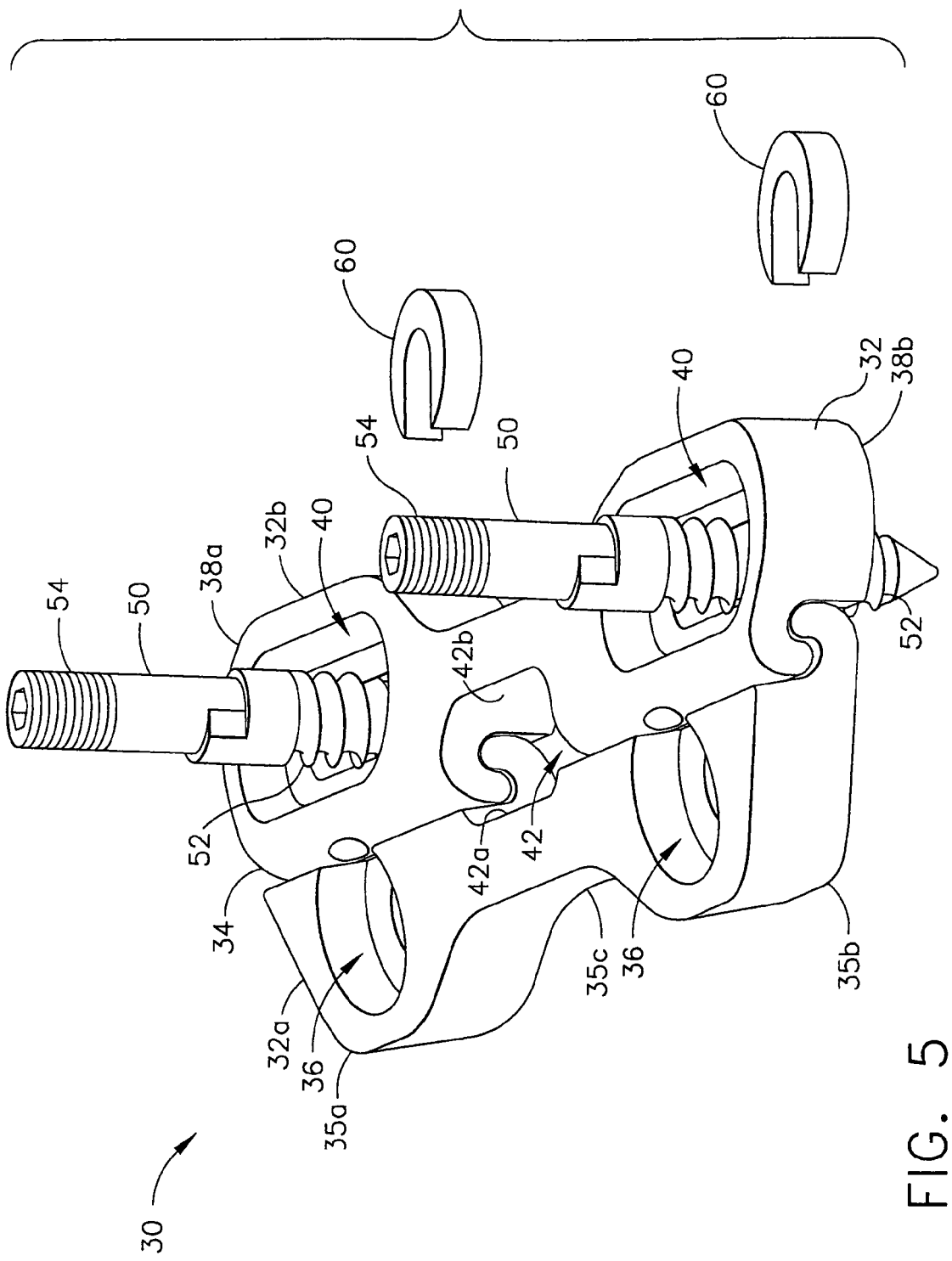
FIG. 5 is a perspective partially assembled view of the spinal plate of the present invention along with C-rings.
Figure 6:
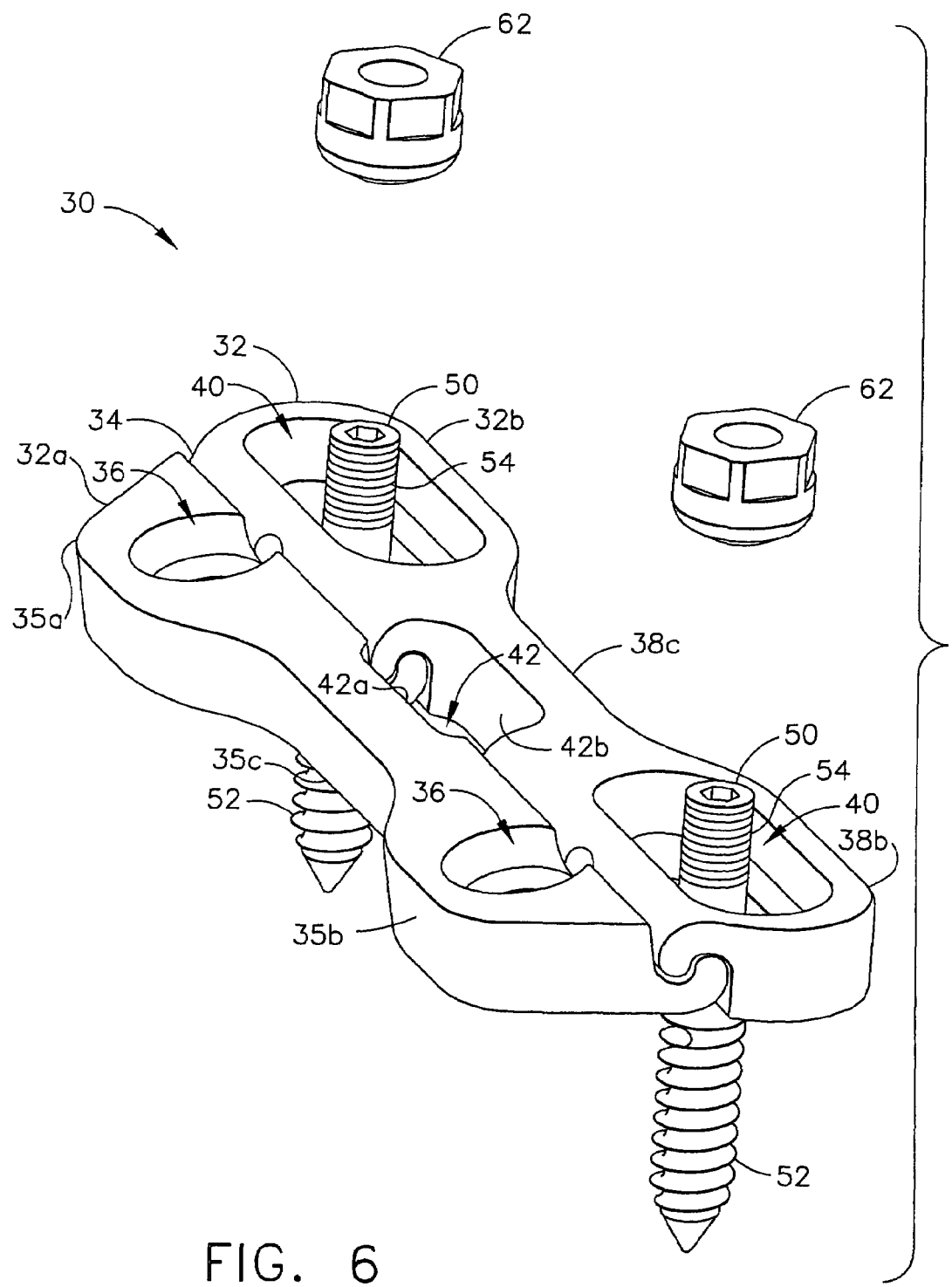
FIG. 6 is another perspective partially assembled view of the system of FIG. 5 along with locking nuts.
Figure 7:
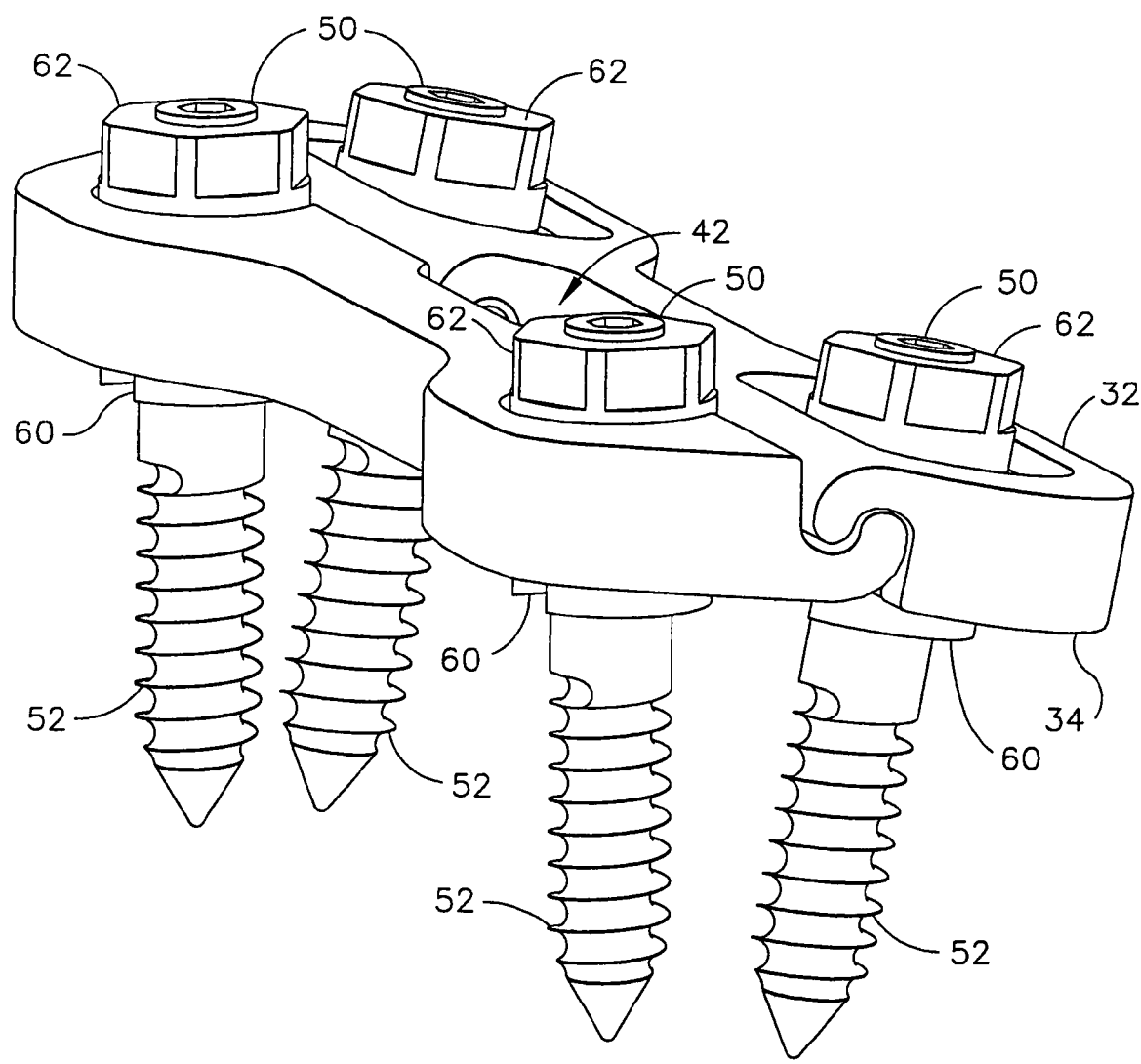
FIG. 7 is a perspective view of the spinal plate system of FIG. 5 in its assembled position.

FIGS. 5-7 show a preferred embodiment of a hinged spinal plate system 30 of the present invention, ideally suited for use in the lumbar/thoracic portion of the spine. Plate system 30 includes a thin plate 32 having two plate elements 32a, 32b which are removably coupled together along a hinged section 34. Element 32a contains generally rounded edges 35a, 35b, a cutaway section 35c, and two generally circular through openings 36 positioned collinearly along element 32a. Element 32b contains generally rounded edges 38a, 38b, a cutaway section 38c, and two generally circular through openings 40 positioned collinearly along element 32b. Although openings 36 on plate element 32a are shown as circular in this embodiment, and openings 40 on plate element 32b are shown as elongated slots, openings 36, 40 may be configured in any suitable combination of circular openings and elongated slots. Cutaway sections 35c, 38c afford the surgeon a better view of the bone graft inserted between vertebrae, in part to insure that the bone graft is not projecting into the spinal cord or nerves. Plate 32 is preferably constructed from an implant grade titanium alloy, such as Ti-6Al-4V. Alternatively, plate 32 may be constructed from any number of suitable materials, such as stainless steel ASTM F138.

An opening 42 is formed along hinged section 34 of plate system 30 by a cutout section 42a in element 32a and a cutout section 42b in element 32b. Opening 42 may be used to accommodate additional hardware to increase the stability of plate system 30 against the spine. Also, opening 42 may be used if additional hardware is needed to secure the bone graft in position.

A series of bolts 50 are inserted through openings 36, 40 to secure plate 32 to the vertebrae. Bolts 50 contain a lower threaded portion 52 for threadedly engaging pre-drilled holes in the appropriate vertebrae of the spine, and an upper threaded portion 54 which extends through plate 32 after it has been installed in its proper position. Bolts 50 contain an unthreaded middle portion located between lower threaded portion 52 and upper threaded portion 54, as such bone-engaging screws are known to and used by those skilled in the art.

A series of snap or C-rings 60 are used with bolts 50 to securely fasten plate 32 in its proper position. Snap or C-rings 60 are clipped onto upper threaded portion 54 of bolts 50 after lower threaded portion 52 has been anchored within the appropriate vertebrae but before plate 32 has been fully installed. Alternatively, snap or C-rings 60 are clipped onto the middle unthreaded portion of bolt 50 in embodiments of plate system 30 utilizing such a bolt 50. Finally, a series of nuts 62 are threaded onto upper threaded portion 54 of bolts 50 to secure plate 32 in its proper position. It is contemplated that alternative embodiments of plate system 30 may employ ordinary washers in place of snap or C-rings 60.

Figure 8:
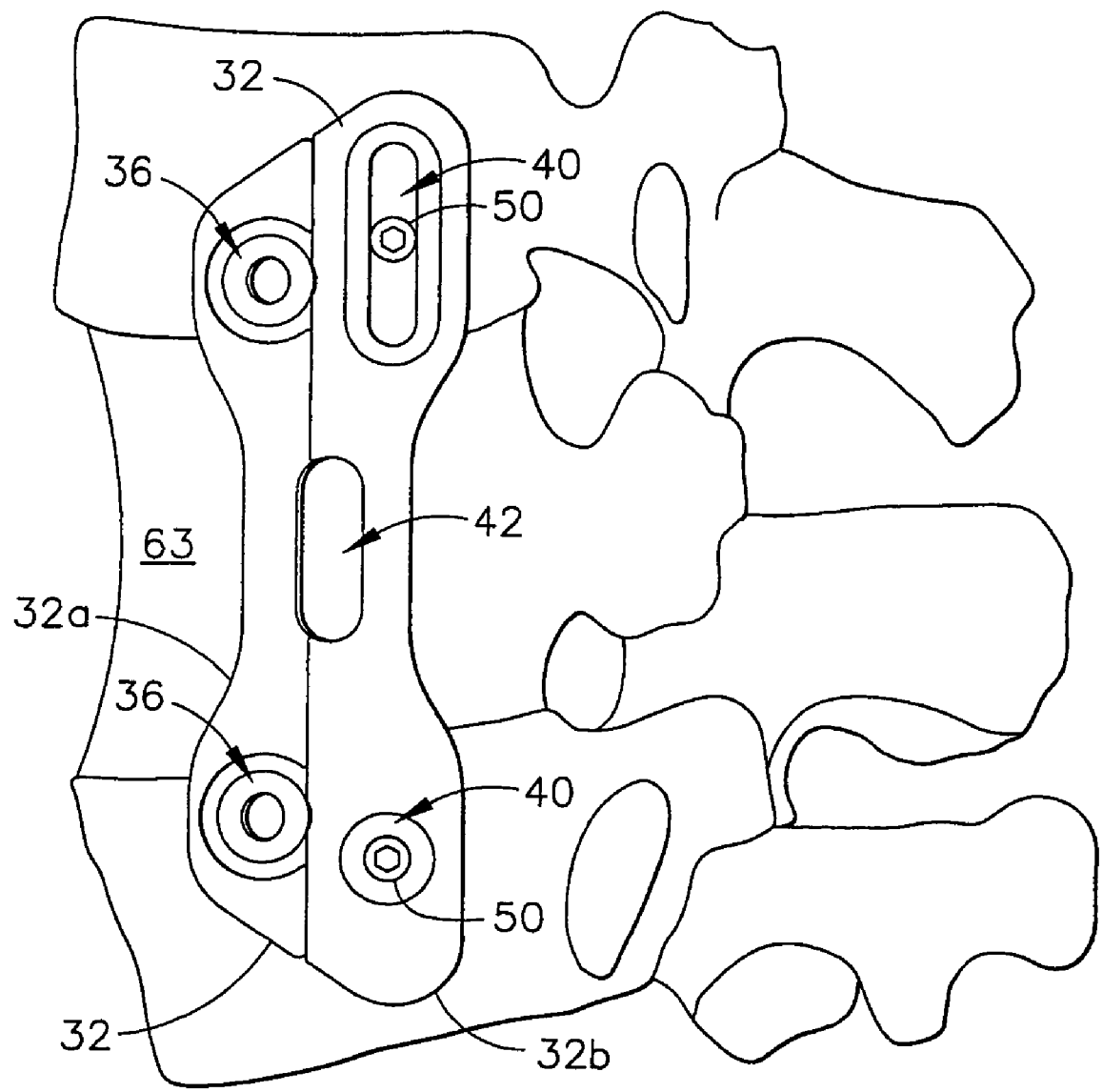
FIG. 8 is a lateral view of the plate system of the present invention with two bolts installed.

The preferred method of using hinged plate system 30 is shown in FIGS. 8-13. Referring to FIG. 8, a bone graft 63 is inserted between vertebrae to serve as a replacement vertebra. After selecting a plate 32 of suitable size, two bolts 50 are affixed within the appropriate vertebrae. To accomplish this, a pair of holes are drilled into the vertebrae at a 15° anterior angulation using openings 40 as a guide. Bolts 50 are then screwed into place through plate 32 to ensure placement in the proper location. Preferably, upper bolt 50 is placed into the cephalad portion of opening 40 as shown in FIG. 8 to allow for compression.

It is conceivable that other fastening systems could be used to secure plate 32 to the spine. By way of example only, several two part screw systems having an outer vertebral screw and a locking inner screw are taught in a patent application entitled ANATOMIC POSTERIOR LUMBAR PLATE, filed in the name of Bret A. Ferree on the same day as this application and hereby incorporated by reference in its entirety. Such screw systems may be used in place of bolts 50 in the present invention, as these two part screws create a "bolt" as understood in relation to the present invention.

Figure 9:
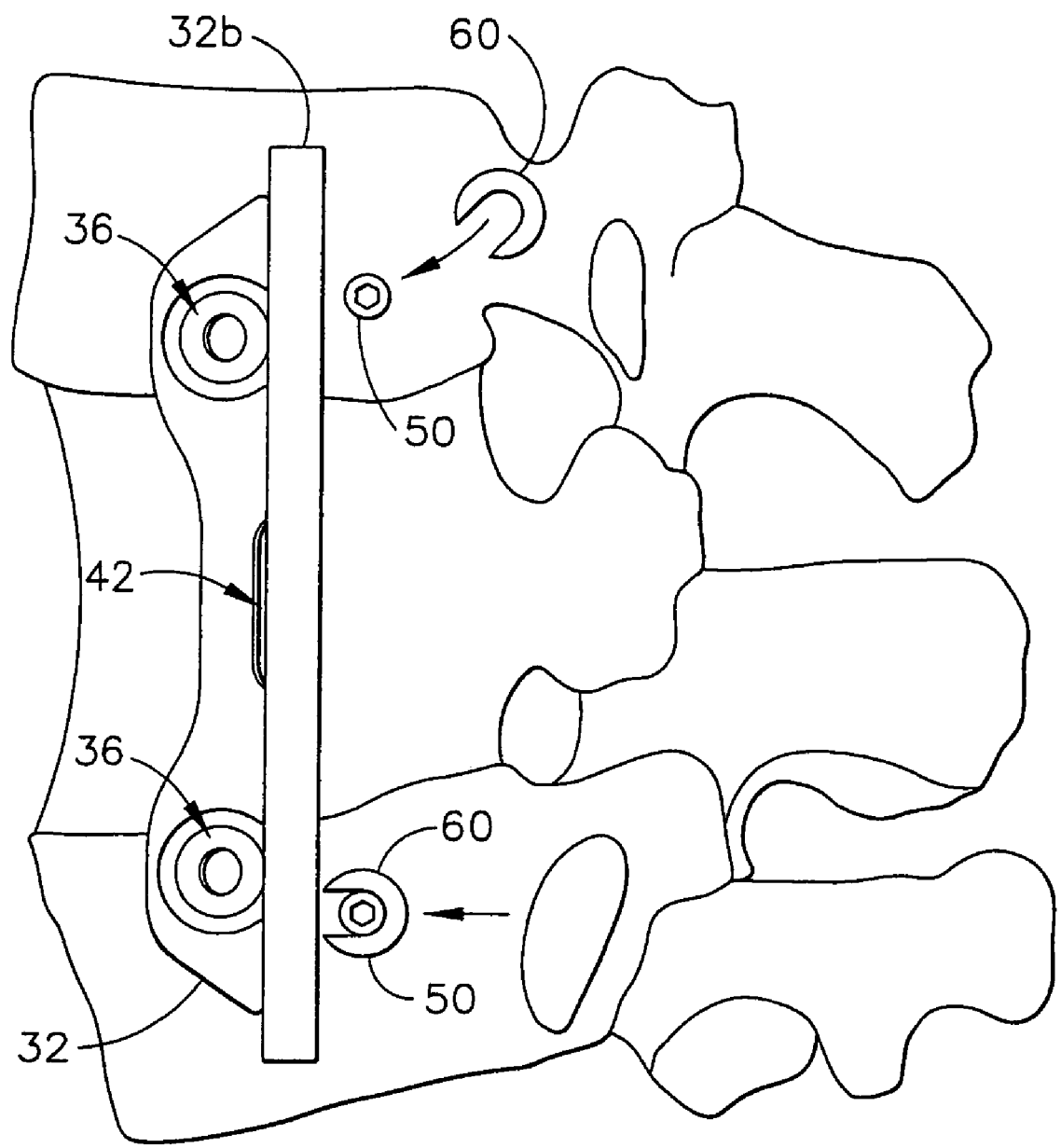
FIG. 9 is a lateral view of the plate system of the present invention during the installation of two C-rings.
Figure 10:
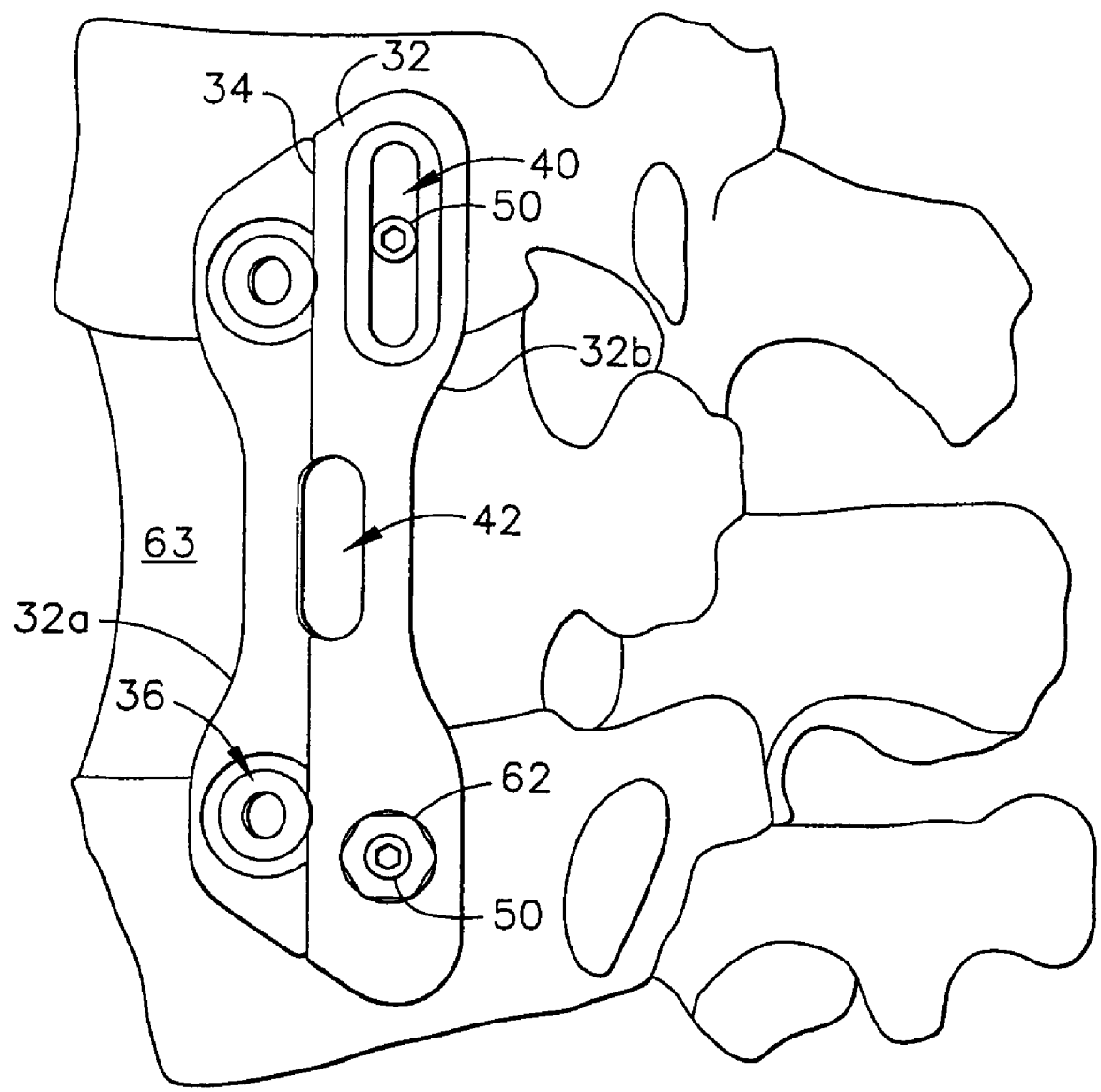
FIG. 10 is a lateral view of the plate system of the present invention with the nut installed on the lower posterior bolt.

As shown in FIG. 9, the next step involves flipping posterior element 32b of plate 32 upwardly away from the vertebrae. In the alternative, posterior element 32b and/or plate 32 may be removed in its entirety. In any case, snap rings 60 are applied to upper threaded portion 54 of bolts 50 to secure them in place. As shown in FIG. 10, posterior element 32b of plate 32 is then repositioned over the two bolts 50, by either flipping downward toward the vertebrae or by reconnecting posterior element 32b to anterior element 32a along hinged element 34. While compressing bone graft 63 between the vertebrae, nut 62 is then applied to upper threaded portion 54 of lower bolt 50, and securely tightened against plate 32. Preferably, the wrench used to tighten nut 62 onto lower bolt 50 is cannulated to allow insertion of a screwdriver or other suitable tool to prevent rotation of bolt 50 while nut 62 is threaded onto upper threaded portion 54 of bolt 50.

Figure 11:
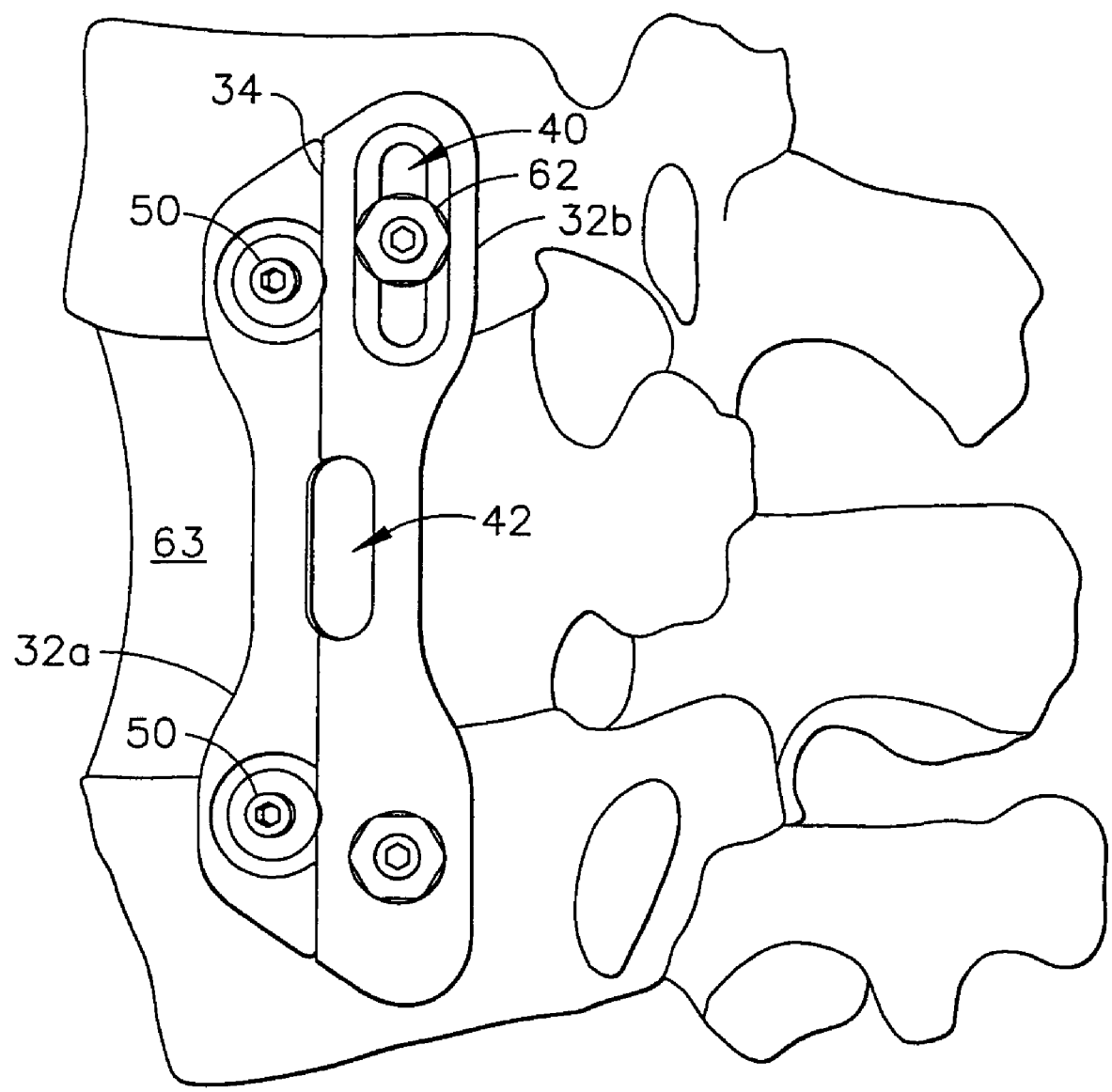
FIG. 11 is a lateral view of the plate system with the two posterior bolts installed.
Figure 12:
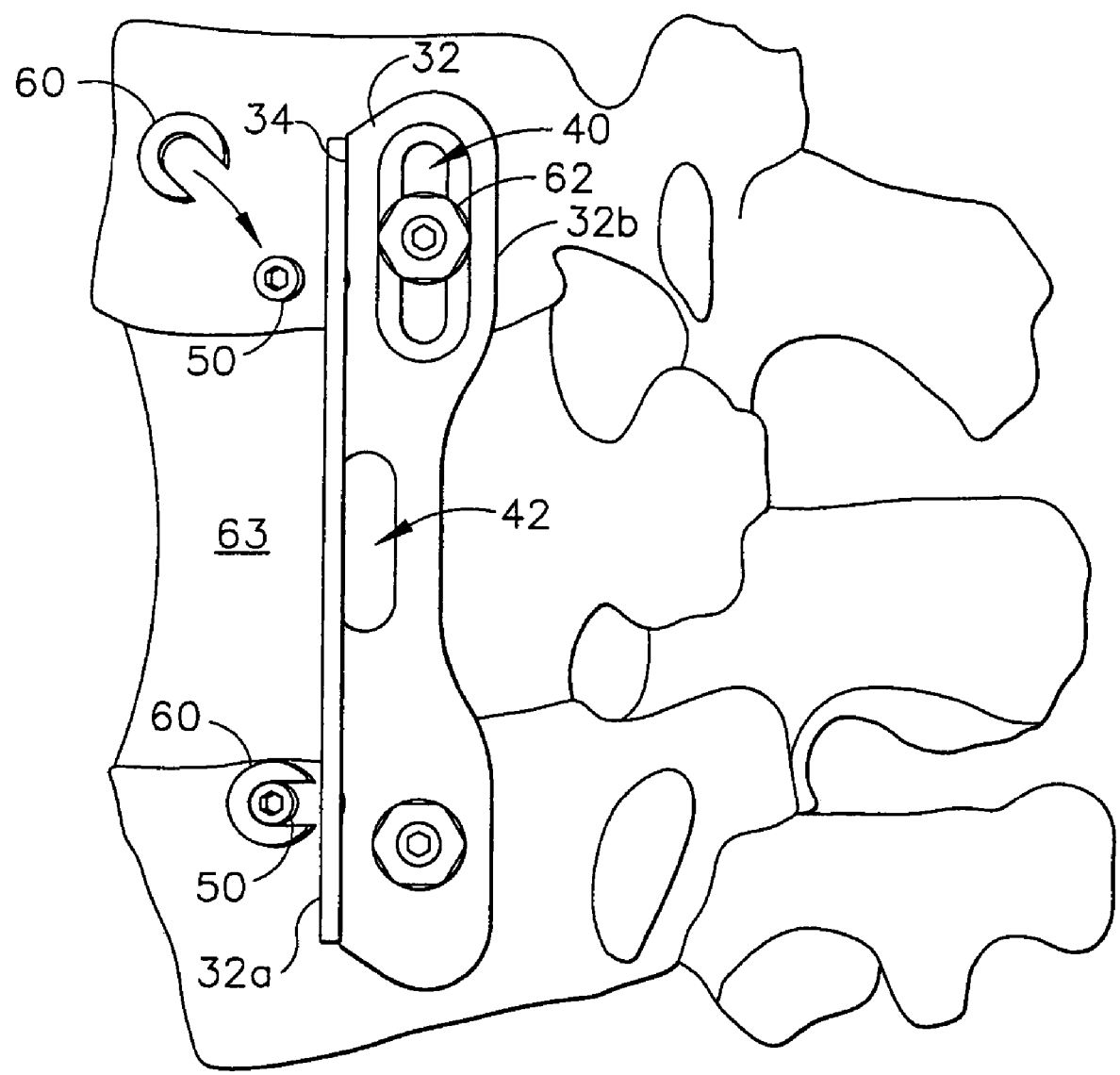
FIG. 12 is a lateral view of the plate system with C-rings for the anterior bolts.
Figure 13:
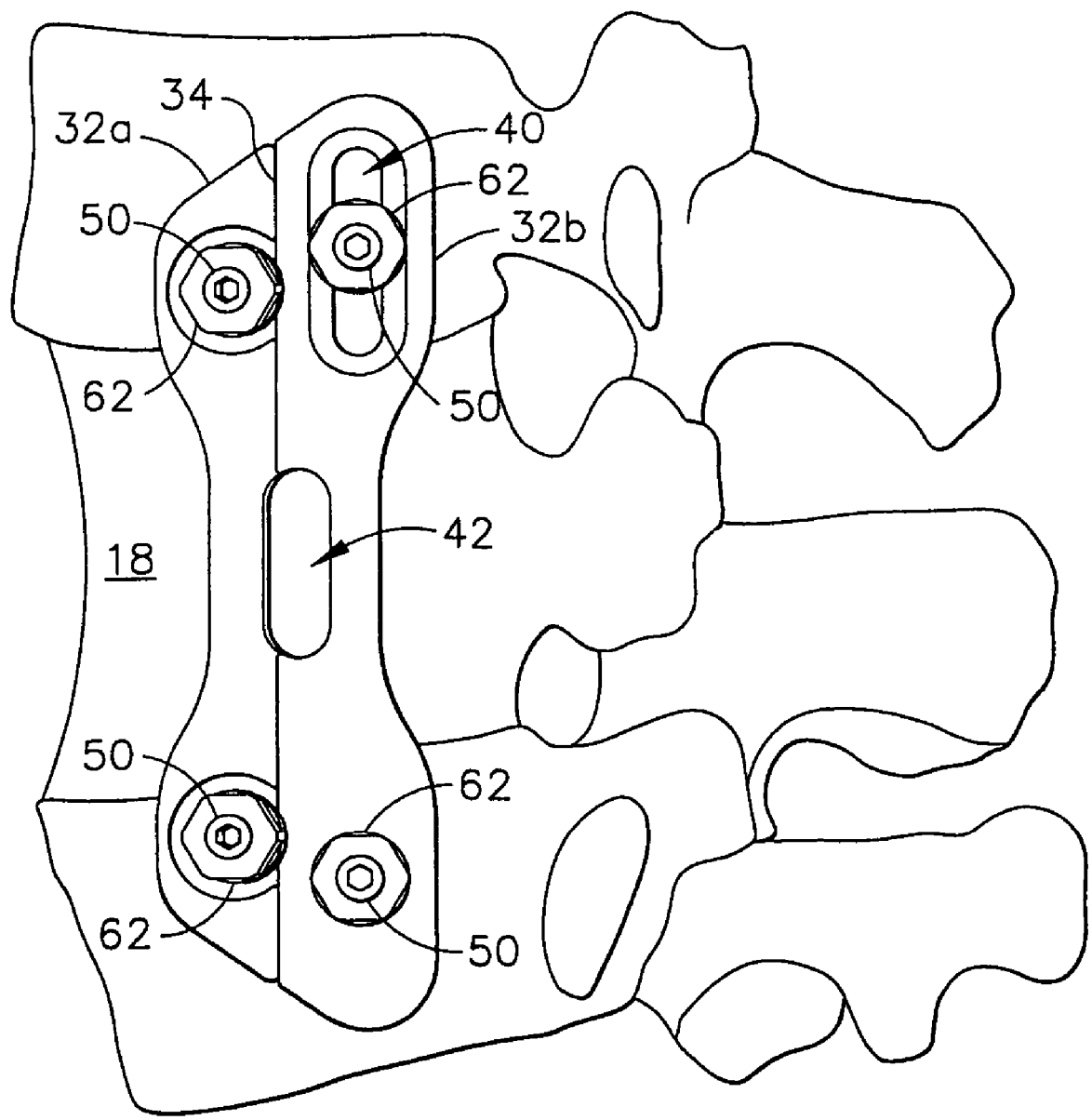
FIG. 13 is a lateral view of the plate system of the present invention completely installed.

With continued reference to FIG. 10, a pair of holes are then drilled into the vertebrae using openings 36 on the anterior element 32a as a guide. Bolts 50 can then be affixed into place through element 32a (FIG. 11). As shown in FIG. 12, anterior element 32a is then flipped upwardly or removed entirely, and snap rings 60 are secured on upper threaded portion 54 of bolts 50. Element 32a of plate 32 can now be returned to its proper position, and nuts 62 are applied to upper threaded portion 54 of bolts 50 and tightened to completely secure plate 32 against the vertebrae, as shown in FIG. 13. Optionally, another screw 70 may be inserted through opening 42 into bone graft 63 (or a cage if one has been inserted).

Figure 14:
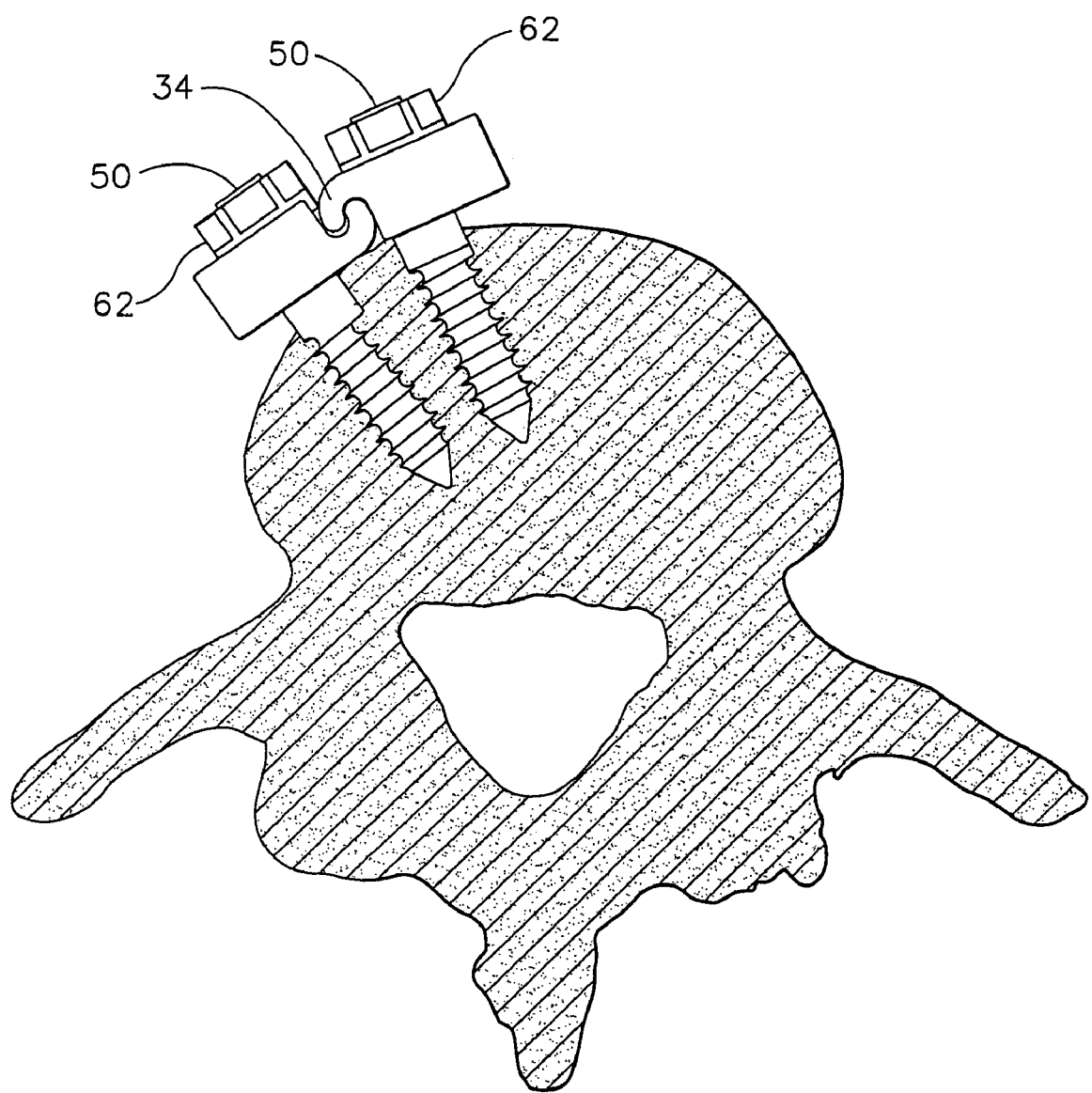
FIG. 14 is a sectional view of the system shown in FIG. 13.

FIG. 14 is a sectional view of a vertebra on which a hinged plate system 30 of the present invention has been installed. Bolts 50 can be seen penetrating the vertebra. The relative angularity between bolts 50 provides the force necessary to securely hold plate system 30 in the proper orientation to promote healing. In addition, hinged section 34 assists to contour plate 32 to the convexity of the vertebrae, allowing plate 32 to more effectively contact the vertebral surface.

Figure 16:
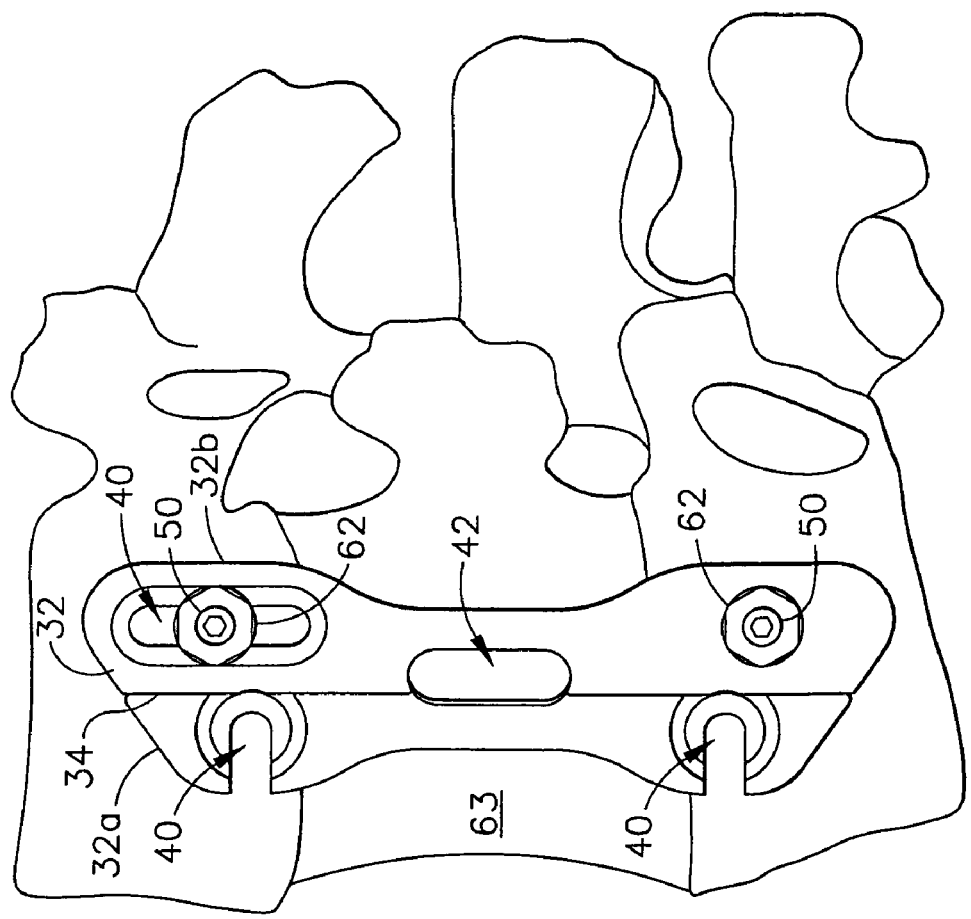
FIG. 16 is a lateral view of the plate system having slotted holes on the anterior section of the plate.
Figure 15:
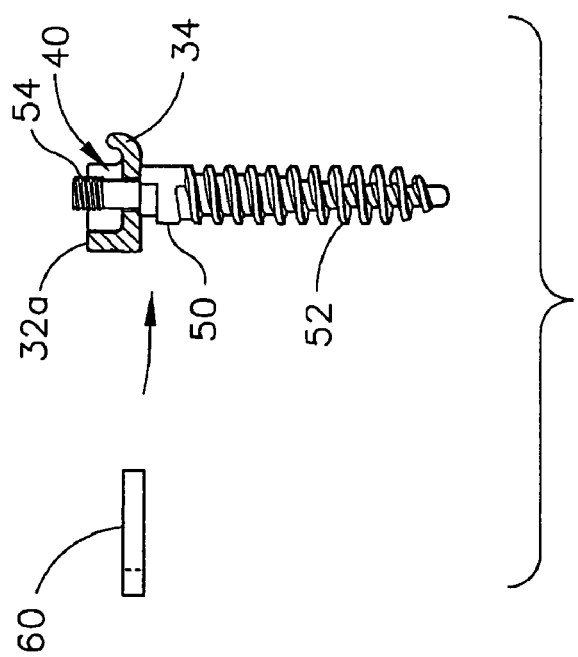
FIG. 15 is a fragmentary view of an anterior hole of plate of the present invention showing the beveled orientation through the plate.

It is contemplated that other modifications could be made to plate 32 in order to simplify the installation process. By way of example only, openings 40 on element 32b may be beveled such that element 32a can be lifted slightly while positioned on upper threaded portion 54 of bolt 50, allowing snap ring 60 to be inserted below plate 32 onto bolt 50 without substantial displacement of element 32a (FIG. 15). FIG. 16 shows a plate 32 in which openings 40 in element 32a are slotted toward rounded edges 35a, 35b such that element 32a can be easily flipped in an upward direction.

Figure 18:
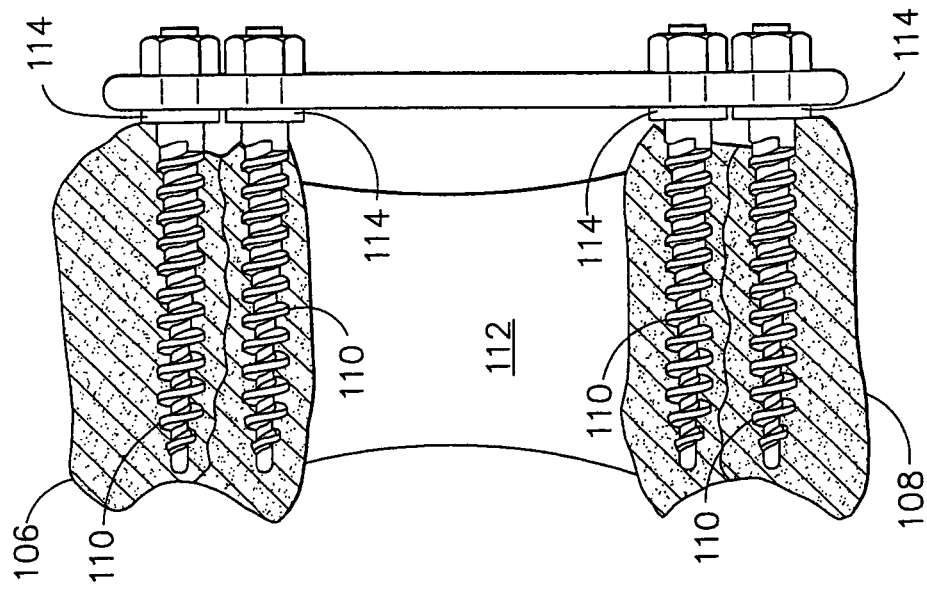
FIG. 18 is a side view of the plate shown in FIG. 17 partly in phantom.
Figure 17:
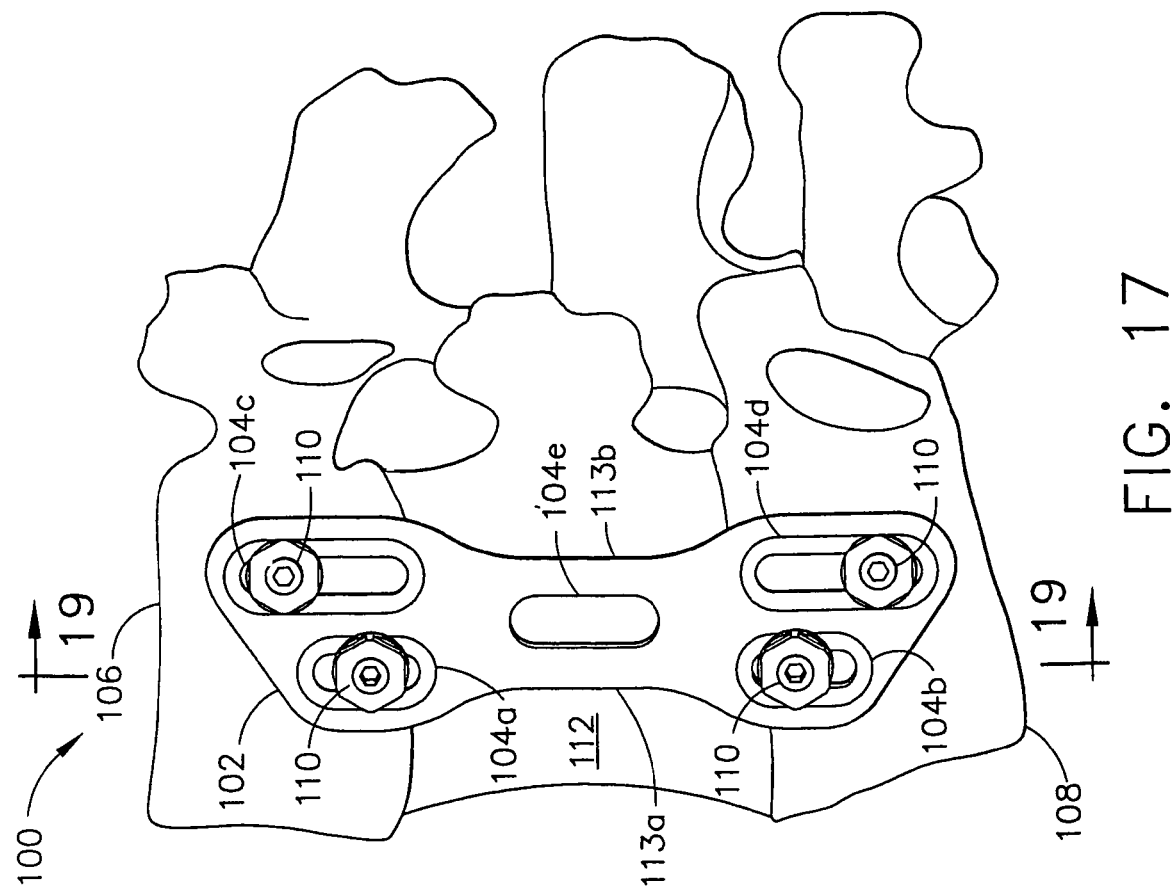
FIG. 17 is a lateral view of an alternative embodiment of the plate system of the present invention.

An alternate embodiment of the spinal plate system of the present invention is shown in FIGS. 17-22. Referring to FIGS. 17 and 18, a spinal plate system 100 is shown mounted in position on the spinal column of a patient. A unitary plate 102 having a plurality of slots 104a-e is fastened by a plurality of bolts 110 as previously described at vertebrae 106, 108. A bone graft 112 has been inserted between vertebrae 106, 108 to serve as a replacement vertebra. Plate 102 contains cutaway edge portions 113a, 113b to allow the surgeon to visualize the bone graft easily. Bolts 110, which are shown mounted through slots 104a-d, are held in place by a plurality of snap-rings 114. Central slot 104e located in the central region of plate 102 may be used for an additional screw or bolt through a central vertebra or bone graft. In addition, the bottom surface of plate 102 may contain a friction surface to allow better contact with the bone structures.

FIG. 19 shows a cross-sectional view of the plate of FIG. 17. Preferably, plate 102 has a thickness of approximately 7 mm, and is curved to allow for better contact with the vertebral surface. Anterior slots 104a, 104b, which each have a preferred width of approximately 7 mm, are substantially perpendicular to the upper and lower surfaces of plate 102. Posterior slots 104c, 104d, which each have a preferred width of approximately 7 mm, are oriented at approximately a 15° anterior angulation between the upper and lower surfaces of plate 102. The preferred length of plate 102 ranges from 60 mm to 100 mm. The preferred width of plate 102 is approximately 20 mm at its widest portion, and approximately 12 mm across cutaway sections 112a, 112b.

Plate 102 can be shaped to more easily fit the spine when used in different areas. FIG. 20 shows a plate 102 which is angled 15° in the forward (i.e. anterior) direction to compensate for kyphotic conditions, while FIG. 21 shows a plate 102 which is angled 15° in the reverse (i.e. posterior) direction to compensate for lordotic conditions. Finally, FIG. 22 depicts a shorter plate 102, which may be used in situations where longer plates are impracticable or unnecessary.

While the present invention has been shown and described in terms of preferred embodiments thereof, it should be understood that this invention is not limited to any particular embodiment, and that changes and modifications may be made without departing from the true spirit and scope of the invention as defined in the appended claims.

What is claimed is:

1. A method of fusing a first vertebral body to a second vertebral body, comprising:
   inserting an implant between a first vertebral body and a second vertebral body; and
   surgically implanting a first plate hingedly coupled to a second plate by permanently affixing said first and second plates to said first and second vertebral bodies to allow said first vertebral body to fuse to said second vertebral body.

2. The method of claim 1, wherein said implant comprises an article of human bone dimensioned for use in spinal surgery.

3. The method of claim 1, wherein said implant comprises a bone graft substitute.

4. The method of claim 3, wherein said bone graft substitute comprises a synthetic bone graft processed from at least one of hydroxyapatite and bone morphogenetic protein.

5. The method of claim 1, wherein said first and second vertebral bodies are at adjacent vertebral levels within the spine.

6. The method of claim 1, wherein said first and second vertebral bodies are not at adjacent vertebral levels within the spine.

7. The method of claim 1, wherein said first and second vertebral bodies comprise vertebrae within at least one of the lumbar and thoracic spine.

8. The method of claim 1, wherein said first and second plates each include at least one pair of openings capable of receiving bone anchor elements for affixing said first and second plates to said first and second vertebral bodies.

9. The method of claim 1, wherein said first plate includes a first hinge element, said second plate includes a second hinge element, and said first and second plates are hingedly coupled together by engaging said first hinge element with said second hinge element.

10. The method of claim 1, wherein affixing said hingedly coupled first and second plates to said first and second vertebral bodies comprises introducing a plurality of bone anchor elements, one through each of a first pair of openings and a second pair of openings to anchor said first and second plates to said first and second vertebral bodies.

11. The method of claim 10, wherein at least one of said first pair of openings and said second pair of openings comprise elongated slots.

12. The method of claim 11, wherein said elongated slots extend along a longitudinal axis of at least one of said first and second plates.

13. The method of claim 10, wherein said second pair of openings lie at a 15° anterior angulation to the upper surface of said second plate.

14. The method of claim 10, wherein said first pair of openings extend to an outer edge of said first plate.

15. The method of claim 10, further comprising a plurality of locking devices which may be fixed in position on said bone anchor elements.

16. The method of claim 15, wherein said locking devices comprise snap rings.

17. The method of claim 10, wherein said bone anchor elements comprise a plurality of bone engaging screws, each of said screws including a lower threaded section for implanting said screw within said bone.

18. The method of claim 17, wherein said screws further include an unthreaded section adjacent to said lower threaded section.

19. The method of claim 18, further including a plurality of locking devices which may be fixed in position on said unthreaded section of said screws.

20. The method of claim 19, wherein said locking devices comprise snap rings.

21. The method of claim 18, wherein said screws further include an upper threaded section adjacent to said unthreaded portion.

22. The method of claim 21, further comprising threadedly engaging a plurality of nuts onto said upper threaded section of said screws.

23. The method of claim 22, further comprising employing a first tool for facilitating said threaded engagement of said nuts onto said upper threaded section.

24. The method of claim 23, wherein said first tool comprises a wrench.

25. The method of claim 23, wherein said first tool is cannulated.

26. The method of claim 25, further comprising inserting a second tool in said cannulated first tool, said second tool preventing rotation of said screw while said nut is threaded onto said upper threaded section.

27. The method of claim 26, wherein said second tool comprises a screwdriver.

28. The method of claim 1, wherein at least one of the first and second plates can be hingedly rotated away from the spine during the plate implantation process.

29. The method of claim 10, further comprising inserting an anchor element into said implant through a third opening.

30. The method of claim 29, wherein said third opening is comprised of a first cutout section from said first plate and a second cutout section from said second plate.

31. The method of claim 29, wherein said third opening is disposed between a first end and a second end of at least one of said first and second plates.

32. The method of claim 29, wherein said anchor element comprises a bone screw.

33. A method of fusing a first vertebra to a second vertebra, each vertebra bisected by a lateral axis so as to include a posterior region and an anterior region, the method comprising:
providing a first plate having a first pair of openings hingedly coupled to a second plate having a second pair of openings; and
surgically implanting said first and second plates to allow said first vertebra to fuse to said second vertebra by permanently affixing said first and second plates to said first and second vertebrae such that said first plate is disposed at least in part within said posterior region of at least one of said first and second vertebrae, and such that said second plate is disposed at least in part within said anterior region of at least one of said first and second vertebra.

34. The method of claim 33, wherein said first and second vertebrae are at adjacent vertebral levels within the spine.

35. The method of claim 33, wherein said first and second vertebrae are not at adjacent vertebral levels within the spine.

36. The method of claim 33, wherein said first and second vertebrae comprise vertebrae within at least one of the lumbar and thoracic spine.

37. The method of claim 33, wherein said first and second pairs of openings are capable of receiving a plurality of bone anchor elements for affixing said first and second plates to said first and second vertebrae.

38. The method of claim 33, wherein said first plate includes a first hinge element, said second plate includes a second hinge element, and said first and second plates are hingedly coupled together by engaging said first hinge element with said second hinge element.

39. The method of claim 33, wherein affixing said hingedly coupled first and second plates to said first and second vertebral bodies comprises introducing a plurality of bone anchor elements, one through each of said first pair of openings and said second pair of openings to anchor said first and second plates to said first and second vertebral bodies.

40. The method of claim 39, further comprising a plurality of locking devices which may be fixed in position on said bone anchor elements.

41. The method of claim 40, wherein said locking devices comprise snap rings.

42. The method of claim 39, wherein said bone anchor elements comprise a plurality of bone engaging screws, each of said screws including a lower threaded section for implanting said screw within said bone.

43. The method of claim 42, wherein said screws further include an unthreaded section adjacent to said lower threaded section.

44. The method of claim 43, further including a plurality of locking devices which may be fixed in position on said unthreaded section of said screws.

45. The method of claim 44, wherein said locking devices comprise snap rings.

46. The method of claim 43, wherein said screws further include an upper threaded section adjacent to said unthreaded portion.

47. The method of claim 46, further comprising threadedly engaging a plurality of nuts onto said upper threaded section of said screws.

48. The method of claim 47, further comprising employing a first tool for facilitating said threaded engagement of said nuts onto said upper threaded section.

49. The method of claim 48, wherein said first tool comprises a wrench.

50. The method of claim 48, wherein said first tool is cannulated.

51. The method of claim 50, further comprising inserting a second tool in said cannulated first tool, said second tool preventing rotation of said screw while said nut is threaded onto said upper threaded section.

52. The method of claim 51, wherein said second tool comprises a screwdriver.

53. The method of claim 33, wherein at least one of said first pair of openings and said second pair of openings comprise elongated slots.

54. The method of claim 53, wherein said elongated slots extend along a longitudinal axis of at least one of said first and second plates.

55. The method of claim 33, wherein said second pair of openings lie at a 15° anterior angulation to the upper surface of said second plate.

56. The method of claim 33, wherein said first pair of openings extend to an outer edge of said first plate.

57. The method of claim 33, wherein at least one of the first and second plates can be hingedly rotated away from the spine during the plate implantation process.

58. A system for performing spinal fusion surgery, comprising:
an implant dimensioned for use in spinal fusion surgery;
a first plate having a first pair of openings dimensioned to receive bone anchor elements and a first cutout section, and a second plate hingedly affixed to said first plate and having a second pair of openings dimensioned to receive bone anchor elements and a second cutout section, wherein said first and second cutout sections in concert comprise a third opening; and
a plurality of bone anchor elements, one for each opening of said first pair of openings and said second pair of openings to anchor said first and second plates to vertebrae in the spine.

59. The system of claim 58, wherein said implant comprises an article of human bone dimensioned for use in spinal surgery.

60. The system of claim 58, wherein said implant comprises a bone graft substitute.

61. The system of claim 60, wherein said bone graft substitute comprises a synthetic bone graft processed from at least one of hydroxyapatite and bone morphogenetic protein.

62. The system of claim 58, wherein said first plate includes a first hinge element, said second plate includes a second hinge element, and said first and second plates are hingedly coupled together by engaging said first hinge element with said second hinge element.

63. The system of claim 58, wherein at least one of said first pair of openings and said second pair of openings comprise elongated slots.

64. The system of claim 63, wherein said elongated slots extend along a longitudinal axis of at least one of said first plate and said second plate.

65. The system of claim 58, wherein said second pair of openings lie at a 15° anterior angulation to the upper surface of said second plate.

66. The system of claim 58, wherein said at least one of said first plate and said second plated is manufactured from titanium.

67. The system of claim 58, wherein said first pair of openings extend to an outer edge of said first plate.

68. The system of claim 58, further comprising a fourth opening disposed between a first end and second end of at least one of said first and second plates.

69. The system of claim 58, further comprising a plurality of locking devices which may be fixed in position on said bone anchor elements.

70. The system of claim 69, wherein said locking devices comprise snap rings.

71. The system of claim 58, wherein said bone anchor elements comprise a plurality of bone engaging screws, each of said screws including a lower threaded section for affixing said screws within bone.

72. The system of claim 71, wherein said screws further include an unthreaded section adjacent to said lower threaded section.

73. The system of claim 72, further including a plurality of locking devices which may be fixed in position on said unthreaded section of said screws.

74. The system of claim 73, wherein said locking devices comprise snap rings.

75. The system of claim 72, wherein said screws further include an upper threaded section adjacent to said unthreaded portion.

76. The system of claim 75, further comprising a plurality of nuts capable of threadedly engaging said upper threaded section of said screws.

77. The system of claim 76, further comprising a first tool for facilitating said threaded engagement of said nuts onto said upper threaded section.

78. The system of claim 77, wherein said first tool comprises a wrench.

79. The system of claim 77, wherein said first tool is cannulated.

80. The system of claim 79, further comprising a second tool for insertion in said cannulated first tool, said second tool preventing rotation of said screw while said nut is threaded onto said upper threaded section.

81. The system of claim 80, wherein said second tool comprises a screwdriver.

* * * * *